United States Patent
Murray (10) Patent No.: US 6,573,055 B2
(45) Date of Patent: Jun. 3, 2003

(54) DETERMINATION OF RECOMBINANT GLYCOSYLATED PROTEINS AND PEPTIDES IN BIOLOGICAL FLUIDS

(75) Inventor: Allen K. Murray, Newport Beach, CA (US)

(73) Assignee: Glycozyme, Inc., Irvine, CA (US)

( * ) Notice: Subject to any disclaimer, the term of this patent is extended or adjusted under 35 U.S.C. 154(b) by 0 days.

(21) Appl. No.: 09/063,983

(22) Filed: Apr. 21, 1998

(65) Prior Publication Data
US 2002/0048783 A1 Apr. 25, 2002

Related U.S. Application Data
(60) Provisional application No. 60/044,154, filed on Apr. 21, 1997.

(51) Int. Cl.[7] .............................................. G01N 33/53
(52) U.S. Cl. ...................... 435/7.1; 436/547; 530/387.5; 530/388.23; 530/389.2
(58) Field of Search .......................... 435/7.1; 436/547; 530/387.5, 388.23, 389.2

(56) References Cited

U.S. PATENT DOCUMENTS

| | | | | |
|---|---|---|---|---|
| 4,703,008 A | * | 10/1987 | Lin | 435/360 |
| 4,954,437 A | * | 9/1990 | Beck et al. | 435/69.4 |
| 5,106,760 A | * | 4/1992 | Egrie | 436/518 |
| 5,324,663 A | * | 6/1994 | Lowe | 435/320.1 |
| 5,419,904 A | * | 5/1995 | Irie | 424/155.1 |
| 5,459,031 A | * | 10/1995 | Blumen et al. | 435/3 |
| 5,621,080 A | * | 4/1997 | Lin | 530/350 |
| 5,661,125 A | * | 8/1997 | Strickland | 514/8 |
| 5,668,679 A | * | 9/1997 | Swearingen et al. | 360/75 |
| 5,695,963 A | * | 12/1997 | McKnight et al. | 435/69.1 |
| 5,756,349 A | * | 5/1998 | Lin | 435/325 |
| 5,856,298 A | * | 1/1999 | Strickland | 514/8 |
| 5,955,422 A | * | 9/1999 | Lin | 514/8 |

FOREIGN PATENT DOCUMENTS

| | | |
|---|---|---|
| EP | 0185870 | 7/1986 |
| EP | 0267678 | 5/1988 |
| WO | WO 91/11529 | 8/1991 |

OTHER PUBLICATIONS

Teshima, G et al, Biochemistry, 1991, vol. 30, pp. 3916–3922.*

Chen, W et al, Mol. Cell Endocrinology, vol. 86(1–2), Jul. 1992, pp. 57–66.*

(List continued on next page.)

Primary Examiner—Lynette R. F. Smith
Assistant Examiner—Ginny Allen Portner
(74) Attorney, Agent, or Firm—Reed Smith Crosby Heafey (57) ABSTRACT

Polyclonal antibodies can be produced that reacts with recombinant EPO and its degradation products but not with native EPO. This antibody precipitation can be used to identify those glycopeptides that are uniquely reactive. These glycopeptides can be produced on preparative scale and used in the production of monoclonal antibodies which are screened against the original EPO and glycopeptides to select antibodies reactive to the specific glycopeptides an recombinant EPO but not to native human EPO. The monoclonal antibodies so selected are incorporated in a conventional ELISA and used to monitor urine and other bodily samples taken from athletes, either human or animal, and patients for presence and level of recombinant peptides or proteins. Alternatively, the polyclonal antibody can be used directly to produce ELISA tests.

2 Claims, 9 Drawing Sheets

Glycopeptide Bound vs. Ab

OTHER PUBLICATIONS

Tanigawara et al, Chem. Pharm. Bull, vol. 38(2), pp. 517–522, 1990.*

Tsuji, J et al. Chem. Pharm. Bull. vol. 38(3), pp. 765–768, 1990.*

Shotton, C et al. J. Virology, Jan. 1995, vol. 69(1), pp. 222–230.*

Noia et al, J. Biological Chemistry, vol. 271(50), Dec. 13, 1996, pp. 32078–32083.*

Sedmak et al, Journal of Interferon Research, vol. 9, Suppl. 1, pp. S61–s65, 1989.*

Doe, B et al, Eur. J. Immunol. vol. 24, 1994, pp. 2369–2376.*

Salmonson, T et al. British J. Clin. Pharm. 1990, vol. 29, pp. 709–713.*

Elliott,S et al. Blood, vol. 87(7), Apr. 1, 1996, pp. 2714–2722.*

Salmonson, T. Scandinavian Journal of Urology and Nephrology, 1990, S129, pp. 1–66.*

Salmonson, T et al. Journal of Internal Medicine, 1990, vol. 228, No. 34, pp. 53–57.*

Kroon, DJ et al, J. Pharm. Biomed. Ana., vol. 13, 1995, pp. 1049–1054.*

Noguchi, A. et al. Nephron, 1996, vol. 72(4), April, pp. 599–603 (English Abstract).*

Zerfaoui, M et al. Eur. J. Clin. Chem. Clin. Biochem. vol. 34, pp. 749–753, 1996.*

Canonne, C. et al, Glycobiology, vol. 5(5), pp. 473–481, 1995.*

Koyama, T et al. J. Haematology, vol. 78, 1991, pp. 515–522.*

Kubach, J et al. J. Chromatography A. vol. 737(2), pp. 281–289, Jun. 21, 1996.*

Inoue, N et al, Biotechnology Annual review, vol. 1, 1995, pp. 297–313.*

Inoue, N et al, Archives of Biochemistry and Biophysics, Mar. 1993, vol. 301(2), pp. 375–378.*

Chen, W et al, Molecular and Cellular Endocrinology, Jul. 1992, vol. 86 (1–2), pp. 57–66 (abstract only), Jul. 1992.*

Inoue, N et al, Biotechnology annual review, vol. 1, 1995, pp. 297–313 (abstract only).*

Inoue, N et al, Archives of Biochemistry and Biophysics, Mar. 1993, vol. 301(2), pp. 375–378 (abstract only).*

Noguchi, A et al, J. Biochem. vol. 117, pp. 59–62, 1995.*

Souillard, a et al, British Journal of Clinical pharmacology, Sep. 1996, vol. 42(3), pp. 355–364.*

Souillard, A et al, Biopharmaceutics and Drug disposition, vol. 17, p. 805–815 (Dec. 1996).*

Koichi Mastsubara et al. "Radioimmunoassay for Erythropoietin using Anti–Recombinant Erthropoetin Antibody with high affinity." p. AB357; XP002081946.

Roger Aston et al. "Monoclonal Antibodies to Human Growth Hormone can Distinguish between Pituitary and Genetically Engineered Forms.", Molecular Immunology, vol. 22, No. 3, Mar. 1985, pp. 271–275, XP002082945, Great Britain..

"Comparative Study of the Asparagine–linked Sugar Chains of Human Erythropoietins Purified From Urine and the Culture Medium of Recombinant Chinese Hamster Ovary Cells", Makoto Takeuchi, et al., *The Journal of Biological Chemistry*, vol. 263, No. 8, Issue of Mar. 15, pp. 3657–3663, 1988.

"Comparative Structural Study of N–Linked Oligosaccharides of Urinary and Recombinant Erythropoietins", Eisuke Tsuda, et al., *Biochemistry*, vol. 27, pp. 5646–5654, 1988.

"Structures and Functional Roles of the Sugar Chains of Human Erythropoietins", Makoto Takeuchi, et al., *Glycobilogy*, vol. 1, No. 4, pp. 337–346, 1991.

Microheterogeneity of Erythropoietin Carbohydrate Structure, Robert S. Rush, et al., *Analytical Chemistry*, vol. 67, No. 8, pp. 1442–1452, 1995.

"Glycosylation Engineering", Pamela Stanley, *Glycobiology*, vol. 2, No. 2, pp. 99–107, 1992.

"Glycosylation of Recombinant Protein Therapeutics: Control and Functional Implications", Dale A. Cumming, *Glycobiology*, vol. 1, No. 2, pp. 115–130, 1991.

"Invited Commentary", Roger A. Laine, *Glyco–Forum Section*, Depts. of Biochemistry and Chemistry, Louisiana State University and the Louisiana Agricultural Center, Baton Rouge, LA 70803 USA, pp. 759–767.

* cited by examiner

DETERMINATION OF RECOMBINANT GLYCOSYLATED PROTEINS AND PEPTIDES IN BIOLOGICAL FLUIDS

The following application is a continuation in part of and claims priority under 35 U.S.C. §119(e) from Provisional Patent Application No. 60/044,154 filed on Apr. 21, 1997, now abandoned.

BACKGROUND OF THE INVENTION

1. Field of the Invention

The present invention is in the field of detection of drugs used for enhancing athletic performance and more specifically in the field of detection of use of natural peptide hormones produced by the techniques of genetic engineering.

2. Background and Description of Related Art

Performance Enhancement

Since the first athletic competition participants have made every attempt to improve and enhance their performance. To the present day this has been done by training, practice, nutrition and striving to maintain good health. Athletes have continued to improve, but there is always the temptation to take "shortcuts," that is, to use various drugs to enhance athletic training and performance. The use of "steroids" by weight lifters and bodybuilders is well known. Similar drugs have also become popular with many other athletes as an aid to training and performance enhancement. Fortunately, many of these compounds are relatively easy to detect in an athlete's blood or other body fluids, thus making steroid use much less attractive. Even difficult to detect steroids are subject to detection by analysis of carbon isotope ratios.

Endurance athletes have been interested in increasing their stamina by "blood doping". Originally, this practice was carried out by collecting and storing the athlete's own blood followed by transfusing the athlete with a concentrate of his or her own red blood cells immediately prior to a competition. This significantly enhances athletic performance by increasing the blood's ability to carry oxygen to the muscles. The downside is that transfusions are cumbersome and require significant medical participation, thereby increasing the chance of detection. Also, the results are rather transitory as the body eliminates the excess red blood cells. Further, the practice is dangerous in that it increases the viscosity of the blood and can lead to cardiovascular disease.

Erythropoietin, a glycoprotein hormone produced in the kidney, one of at least 20 polypeptide factors that control blood cell formation (1), stimulates the production of red blood cells by bone marrow and can produce the effects of "blood doping" with no need for painful transfusions. All that is required is a tiny injection of EPO[1] every few days. However, until recently EPO had to be purified from human urine and was, hence, costly and virtually unavailable. However, availability of recombinant proteins produced for therapeutic medical purposes has become a reality in recent years. Although there are only a handful of recombinant proteins/drugs on the market presently, there are over 100 such products at various stages of the FDA approval process. Unfortunately, the current commercial availability of EPO produced by recombinant DNA techniques has provided an easy means for the athlete who wishes to participate in "blood doping". In fact, a U.S. patent has even been granted on a process to increase the hematocrit of a normal mammal through the use of EPO (U.S. Pat. No. 5,541,158). Furthermore, it is quite possible that recombinant products (e.g., the various human growth hormones) other than EPO will also have the potential for abuse by athletes so that the methods disclosed herein are applicable to situations other than EPO administration.

[1] Abbreviations: BHK: baby hamster kidney, CHO: Chinese hamster ovary, EPO: erythropoietin, uHuEPO: urinary human EPO, rHuEPO: recombinant human EPO, LacNAc: N-acetyllactosamine; HPAEC-PAD: high pH anion-exchange chromatography with pulsed amperometric detection; ELISA: enzyme linked immunoassay.

There are presently no reliable methods available for detecting the abuse of EPO by athletes. There is sufficient indication in the sports medicine literature to strongly suggest that athletes may, in fact, be abusing EPO (2–4). A great deal of interest in the swimming community has resulted from a strong suggestion that the Chinese women swimmers may be using a number of performance enhancing substances including EPO (9). A number of investigators have measured EPO levels in trained athletes, untrained controls, before and after competition in trained athletes (5–8) with varied results. It has been suggested that some of the variability may be due to problems with the bioassay for EPO activity as well as individual variability in the population. This could pose a significant problem in detecting artificially administered EPO because it is likely to be impossible to prove that a high level of EPO is a result of "blood doping" as opposed to a naturally high level. In fact, individuals with "athletic ability" might inherently have a higher endogenous EPO level.

Erythropoietin:

The structure and function of the carbohydrate side chains of Erythropoietin have been the subject of extensive investigation (10–17). Erythropoietin is known to have three N-linked oligosaccharide chains [at asparagine 24, 38, and 83] and one O-linked oligosaccharide chain per molecule [at serine 126]. The carbohydrate side chains make up almost 40% of the total mass of the molecule. At least ten different sugar chain structures have been determined for the asparagine-linked side chains of human erythropoietins and at least four different sugar chain structures have been determined for the O-linked side chains on serine 126. The structures of the N-linked sugar chains of rHuEPO have been well characterized. However, the structures of the mucin-type chains of uHuEPO have not been as well characterized as the N-linked chains.

Differences in the molar ratio (%) of ten different N-linked side chains were summarized in a review by Takeuchi and Kobata (10). They presented data for a biantennary, four triantennary, two tetraantennary side chains and three tetraantennary side chains with 1, 2, and 3 LacNAc repeating units. Past work has demonstrated differences in the oligosaccharide chains of the recombinant EPO and endogenous EPO (11–18). In addition to the carbohydrate differences discussed above, there are also differences in the sialic acid linkages due to the deficiency of a specific sialyltransferase in CHO cells which are used for the expression of the recombinant protein (15).

Principles Behind Present Invention:

The present invention is possible because the DNA for a protein only codes for the primary amino acid sequence of that protein. If such a protein is a glycoprotein, then one can state a priori that the DNA for the protein does not code for the carbohydrate side chains of that glycoprotein although the peptide sequence may determine the sites of glycosylation. Thus, the glycosylation of a recombinant gene product is dependent on the glycosylation machinery of the cell line in which the gene is expressed. In essence, glycosylation is dependent on the array of glycosyltransferases and pools of sugar nucleotide precursors available in the expressing cells.

It has been well documented that, in the case of recombinant glycoproteins, the nature of the carbohydrate side chains is dependent on the cell line in which the glycoprotein is produced and variables in the culture conditions (19, 20). Since it is virtually impossible that tissue culture and human cells in an intact individual would have identical transferases and precursor pools, a given glycosylation pattern can potentially act as a fingerprint for the source of a glycoprotein. The heterogeneity of glycoproteins that is the result of variations the carbohydrate moieties of glycoproteins has given rise to the term glycoforms to describe the multiple forms of the same glycoprotein (i.e., the peptide sequence is the same).

Thus, one or more glycosylation sites on a recombinant peptide may have carbohydrate chains that are not present on the endogenous glycopeptide/glycoprotein. Although sugar groups are often considered "nonantigenic," antibodies can in fact be produced under some conditions. For example, the glycopeptides can be conjugated to bovine serum albumin or Keyhole Limpet Hemocyanin (KLH) to increase their antigenicity. Either polyclonal and monoclonal antibodies to the isolated glycopeptide can then be produced. The resulting library of antibodies can then be screened for ability to recognize the desired glycopeptide. Next the antibodies that recognized the glycopeptide can be screened for those that recognize the intact recombinant molecule. Finally, those antibodies that recognize the desired glycosylated site on the intact recombinant molecule can be tested to determine if they recognize the endogenous glycoprotein molecule, in the case of EPO uHuEPO. At that point, the selection process identifies antibodies that recognize the carbohydrate chain that is unique to the recombinant molecule but that do not recognize the endogenous molecule. These antibodies can then be used to make an enzyme-linked immunoassay kit (ELISA) which recognizes only administered recombinant EPO and ignores endogenous, natural EPO or any other antibody-based detection method can be used.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method of distinguishing recombinant peptides from native peptides.

The microheterogeneity of rHuEPO has been investigated by capillary electrophoresis (21, 22). The separations there were based on the molecular charge heterogeneity of EPO in serum. Capillary electrophoresis may be a good means to differentiate between rHuEPO and endogenous EPO; however, it does not have the sensitivity that is potentially available by ELISA. This means that electrophoresis is unlikely to be useful in monitoring urine and other body fluids, at least without significant concentration of glycopeptides prior to assay In addition, ELISA has an advantage over capillary electrophoresis from the standpoint of being applicable to testing large numbers of samples in standard 96-well titer plates.

In the case of testing for evidence of administration of the particular recombinant protein, as EPO, an ELISA approach can enable the detection of telltale glycoproteins without any requirement for biological activity. This would enable one to detect administration of a recombinant glycoprotein even though biological activity may have already been lost as in the case of urinary excretion products. The serum half-life of administered rHuEPO has been determined by the detection of EPO activity and it has been determined to be on the order of hours, i.e.: 180 min. (23). Since the present approach is not dependent on activity, it is possible that the serum half-life of the detected determinant may, in fact, be longer than that determined for EPO detected by biological activity. Since HuEPO is obtained by isolation from urine, it should also be possible to detect intact rHuEPO in urine by this method as well as inactive or partially degraded rHuEPO. Such degradation products include glycopeptides which are detectable by the method of the present invention. Thus, the time period over which one can detect evidence of rHuEPO administration may, in fact, be longer than that based on direct detection in the blood.

The use of high-pH anion-exchange chromatography (HPAEC-PAD) has become routine for the analysis of glycans in recent years. Further, rHuEPO, expressed in BHK cells, has been used as an example to demonstrate the reliability of this method for the establishment of a mapping database (14). The present invention does depend on the ability to specifically detect low concentrations of oligosaccharides. Currently, there are at least two commercially available detection systems that can be used in the method of the present invention.

1. Dionex Corporation makes the Bio LO system, an HPLC with Pulsed Amperometric Detection. In addition to other extraction and analytical systems, Dionex is also manufacturer of Capillary Electrophoresis instrumentation. Dionex is presently developing a Capillary Electrophoresis unit with a Pulsed Amperometric Detector for carbohydrate detection analogous to that for HPAEC-PAD. Although their "traditional" instruments are useful in the present invention, this new device may be ideally adapted to the present invention.

2. Oxford GlycoSystems (UK) has developed two instruments for carbohydrate analysis to date. One is an automated hydrazinolysis instrument for the selective release of either N-linked or O-linked oligosaccharides. The other unit is an automated system for the sequencing of oligosaccharides. In addition, Oxford GlycoSystems provides oligosaccharide substrates and analytical detection kits for glycobiology. All of these are useful in the practice of the present invention.

A major advantage of the present invention is that the potential for interference by some other glycopeptide marker is extremely remote. For such an event to take place, the individual would have to be receiving another recombinant protein/drug that would have to be produced in CHO cells and it would have to have an identical oligosaccharide on an identical peptide sequence for a few residues on either side of the asparagine for N-linked or serine for O-linked oligosaccharides. Even if the individual were receiving more than one recombinant drug, it is likely that the glycopeptides would be sufficiently different to avoid interference.

Figure 1:
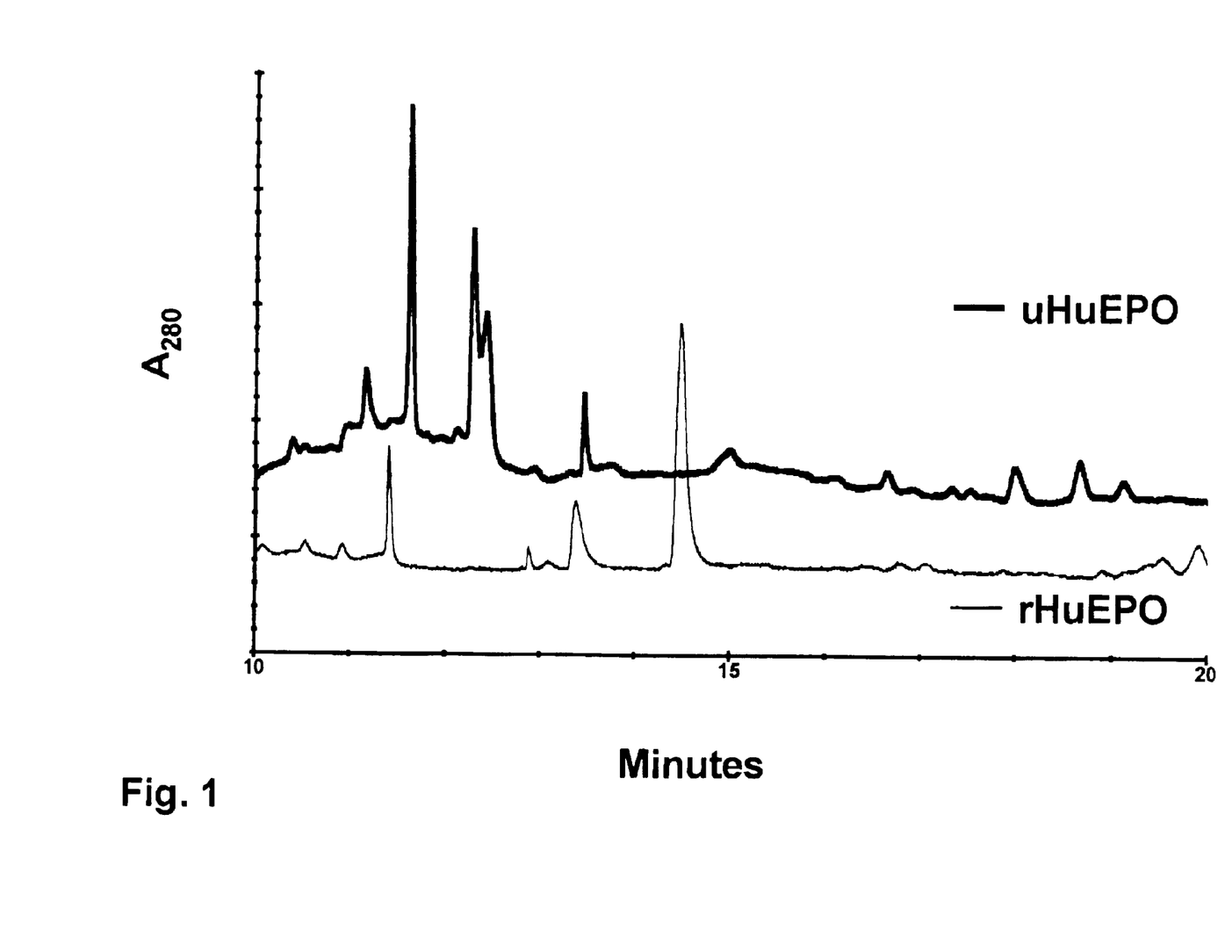
FIG. 1 shows a chromatographic profile of uHuEPO versus rHuEPO as measured by UV absorption.
Figure 2:
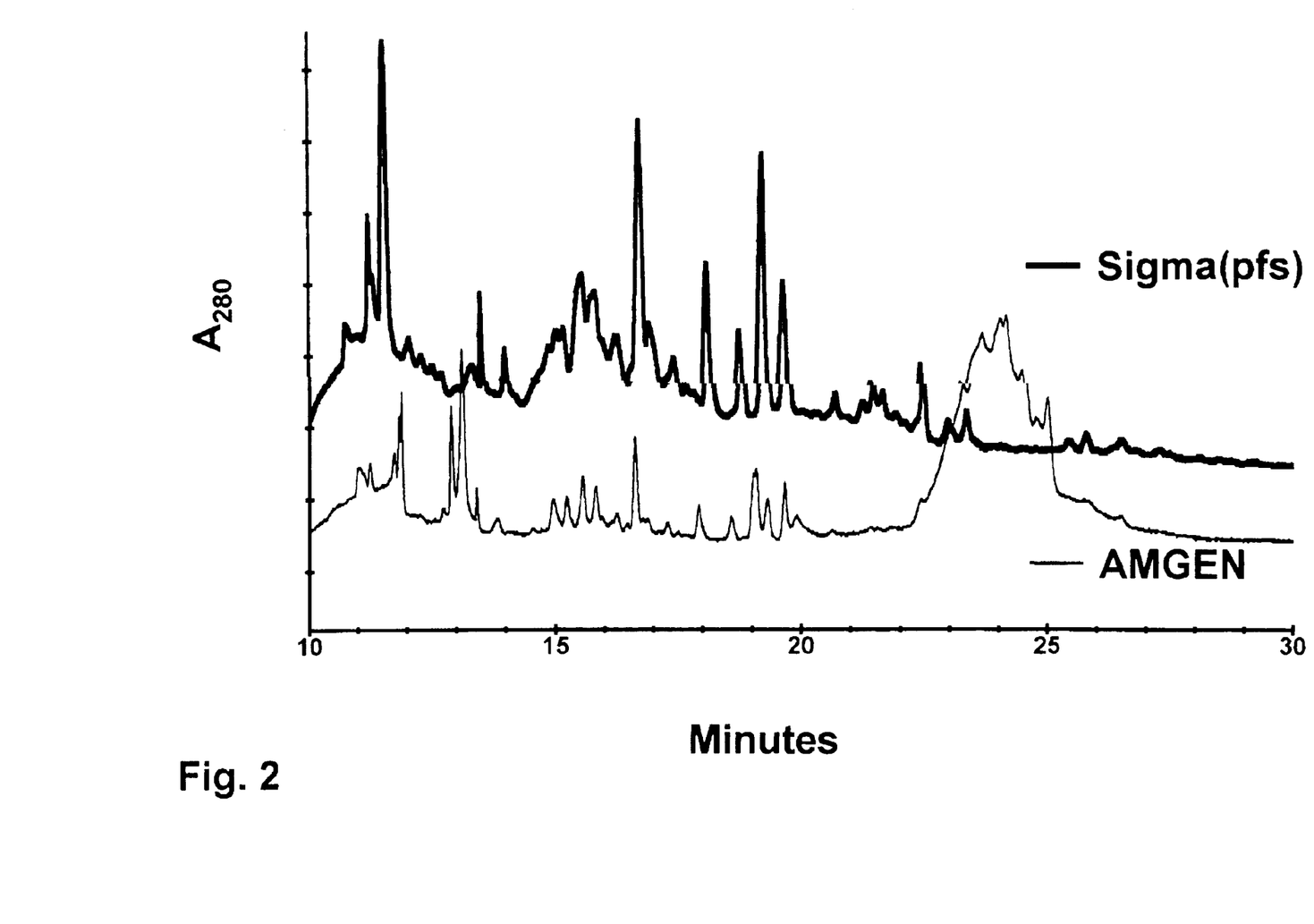
FIG. 2 shows a chromatographic profile of rHuEPO from different sources as measured by UV absorption.

In the method of the present invention uHuEPO and rHuEPO are first fractionated by HPLC at pH 5.0 with detection both on the basis of absorbance at 280 nm to detect protein and detection by PAD (Pulsed Amperometric Detection) at high pH to detect carbohydrates (24). FIG. 1 shows the oligosaccharide profiles of uHuEPO and rHuEPO produced in this manner to demonstrate significant differences. FIG. 2 shows a similar analysis of rHuEPO from two different sources to demonstrate the "fingerprinting" ability of the present approach. These profiles were produced by chromatography on a Dionex NucleoPac PA-100 column at pH 9.5 in 20 mM Tris using a NaCl gradient of from 0% (5 min) to 100% (40 min).

Figure 3:
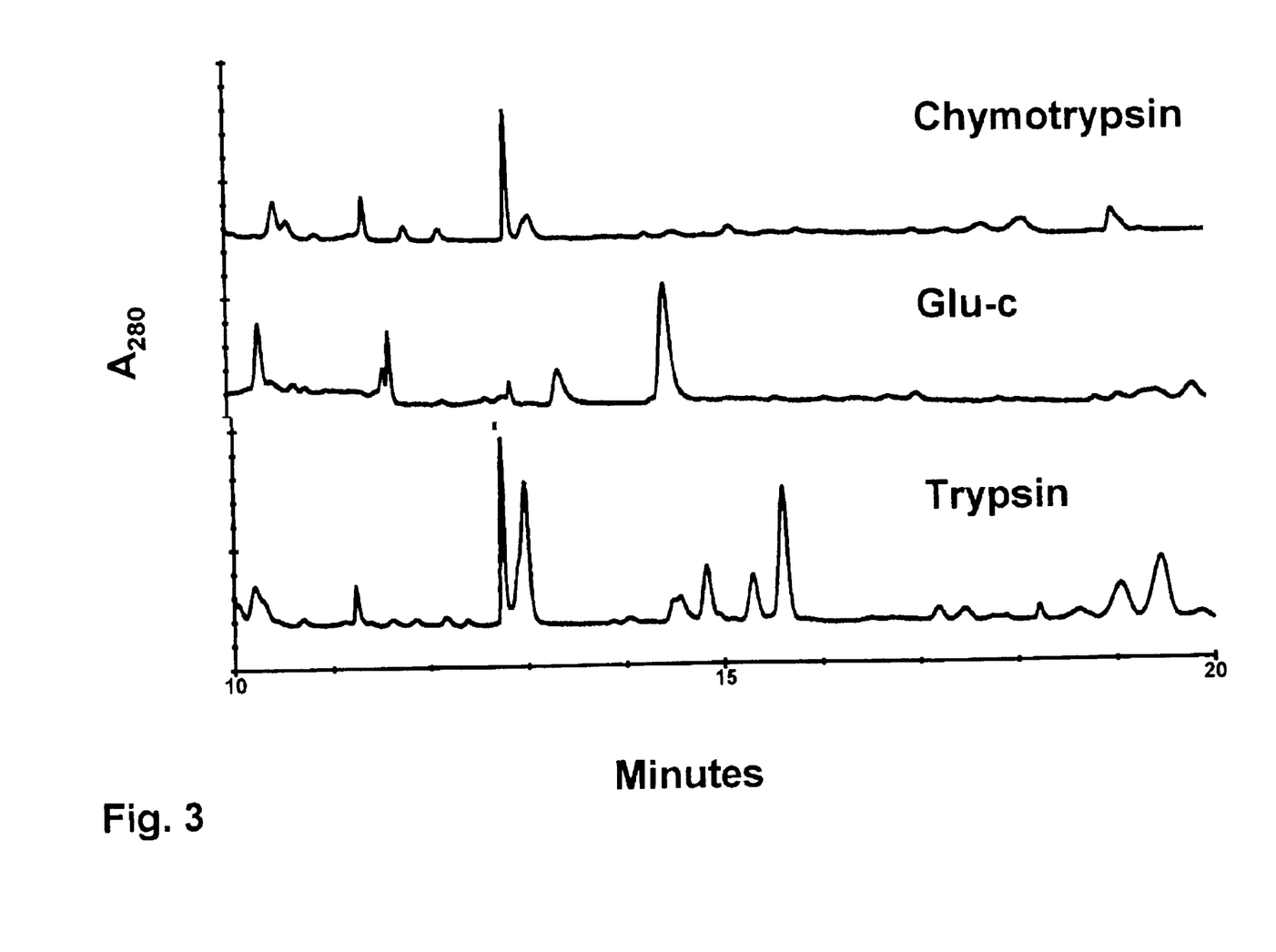
FIG. 3 shows the glycopeptides produced by incubation of rHuEPO in various peptidases.

Since it is likely that degradation products will be present in urine and other body fluids, glycopeptides were generated by treatment of both the uHuEPO and rHuEPO with peptidases which cleave peptide bonds with known specificity. The glycopeptide were also separated by HPAECPAD. FIG. 3 shows the glycopeptides produced after overnight incubation with one of three different proteases (chymotrypsin, trypsin, and Glu-c). The differences shown are due to cleavage site differences whereby different oligosaccharides wind up on different peptide fragments depending on the specific protease. This type of analysis showed that Glu-c digestion of rHuEPO produces fragment distinct from those produced by either trypsin or chymotrypsin digestion.

Figure 4:
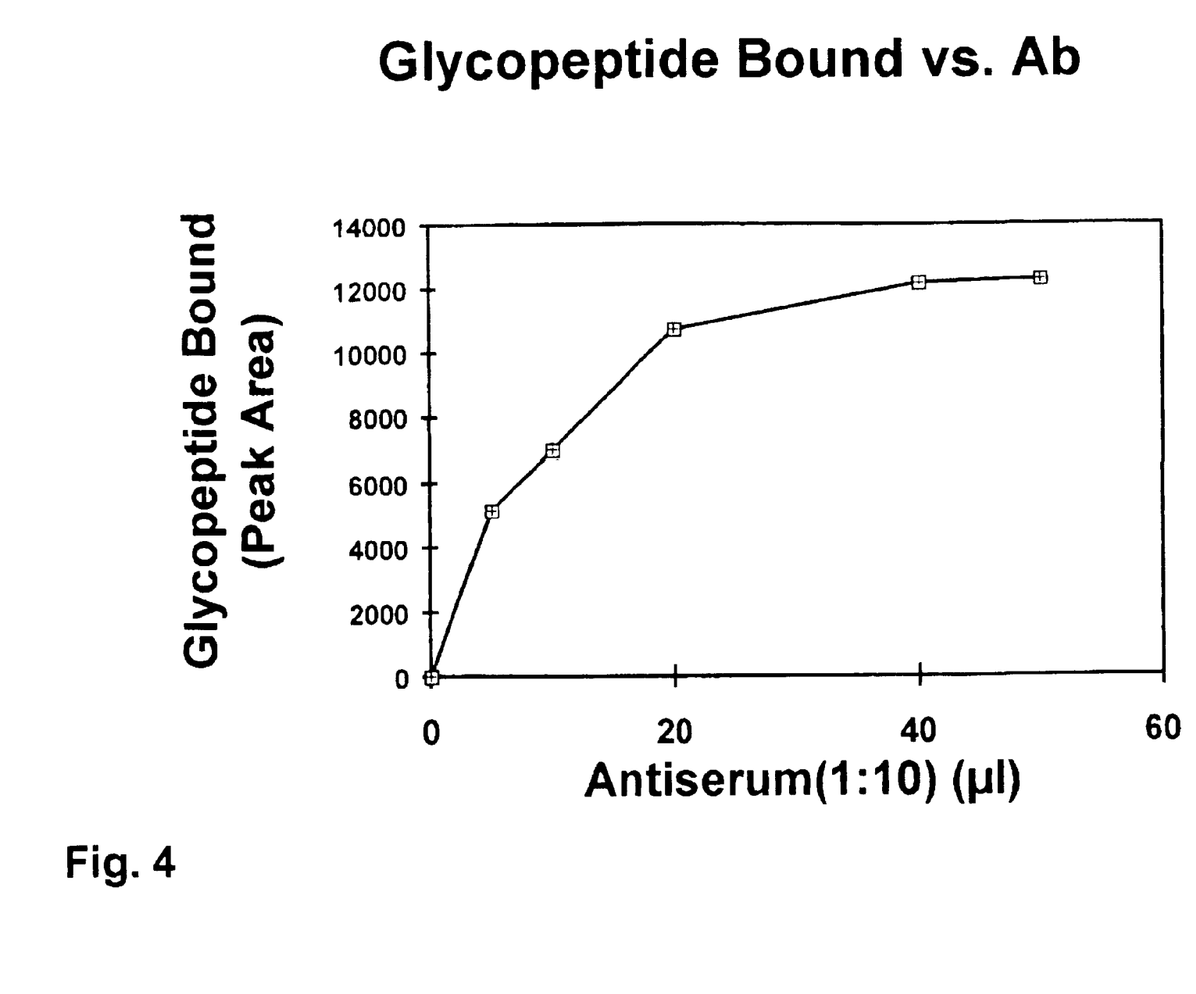
FIG. 4 shows the ability of a polyclonal antibody to precipitate rHuEPO.

Polyclonal antibodies were then raised in rabbits following conventional methods. The animals were immunized with rHuEPO produced by AMGEN. The commercial product was originally stabilized with Human Serum Albumin (HSA). HSA.-free EPO has since become available and is now being used for immunization. However, the initial antibodies produced showed, as expected, considerable reactivity towards HSA. This was resolved by immunizing another animal using HSA-free material. Alternatively, the HSA specificity can be removed using traditional adsorption methods. The resulting polyclonal antibody showed significant ability to precipitate glycopeptides as is shown in FIG. 4. It was somewhat unexpected that the rHuEPO proved so antigenic in rabbits. Much more important is that discovery that the purified rabbit antibody showed little or no reactivity against uHuEPC) or its glycopeptides (data not shown). In retrospect, it seems likely that this surprising outcome is a result of "self-tolerance." Rabbit EPO and human EPO are very similar. The rabbit is naturally unable to produce antibodies against its own EPO. This phenomenon is sometimes known as "tolerance" and in this case is probably a result of the animal being depleted in T cell clones that are responsive to rabbit EPO. Because rabbit and human EPO are so similar, these same clones are necessary for a response to human EPO. For this reason the rabbit is unable to produce antibodies against human EPO peptide. But the CHO oligosaccharides are sufficiently different from native rabbit EPO so as to provoke an immune response. It is likely that the same phenomena will occur when rHuEPO is used as an antigen to produce monoclonal antibodies using standard methods. Should the polyclonal antibody produced in this manner show reactivity to native EPO, standard absorption methods can be used to remove this reactivity leaving only reactivity to the recombinant immunogen. However, the present invention also provides a way of defining particularly effective glycopeptide fragments that may prove even more effective as antigens for raising monoclonal antibodies.

Figure 5A:
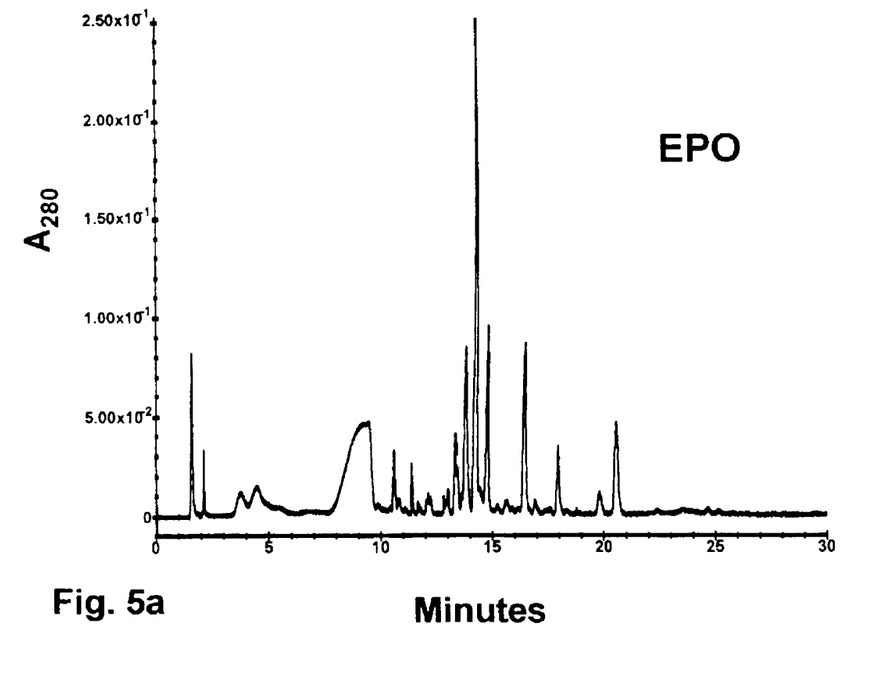
FIG. 5a shows a chromatographic profile of rHuEPO as measured by UV absorption.
Figure 5B:
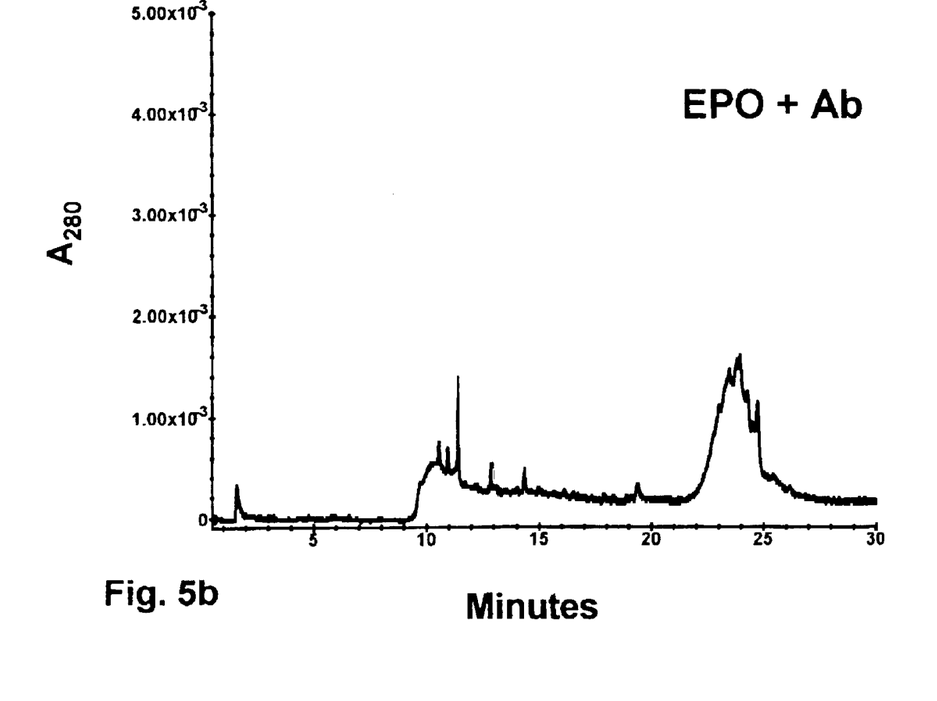
FIG. 5b shows the profile of the material of FIG. 5a following incubation with a polyclonal antibody.

FIG. 5a represents the glycopeptide profile of rHuEPO produced in a manner similar to FIG. 1. FIG. 5b shows this same preparation after incubation with the rabbit polyclonal antibody produced according to the method of the present invention. Notice that the entire pattern is changed showing strong reaction between the antibody and the rHuEPO. Under similar conditions the uHuEPO shows little or no reaction with the antibody (data not shown).

Figure 6:
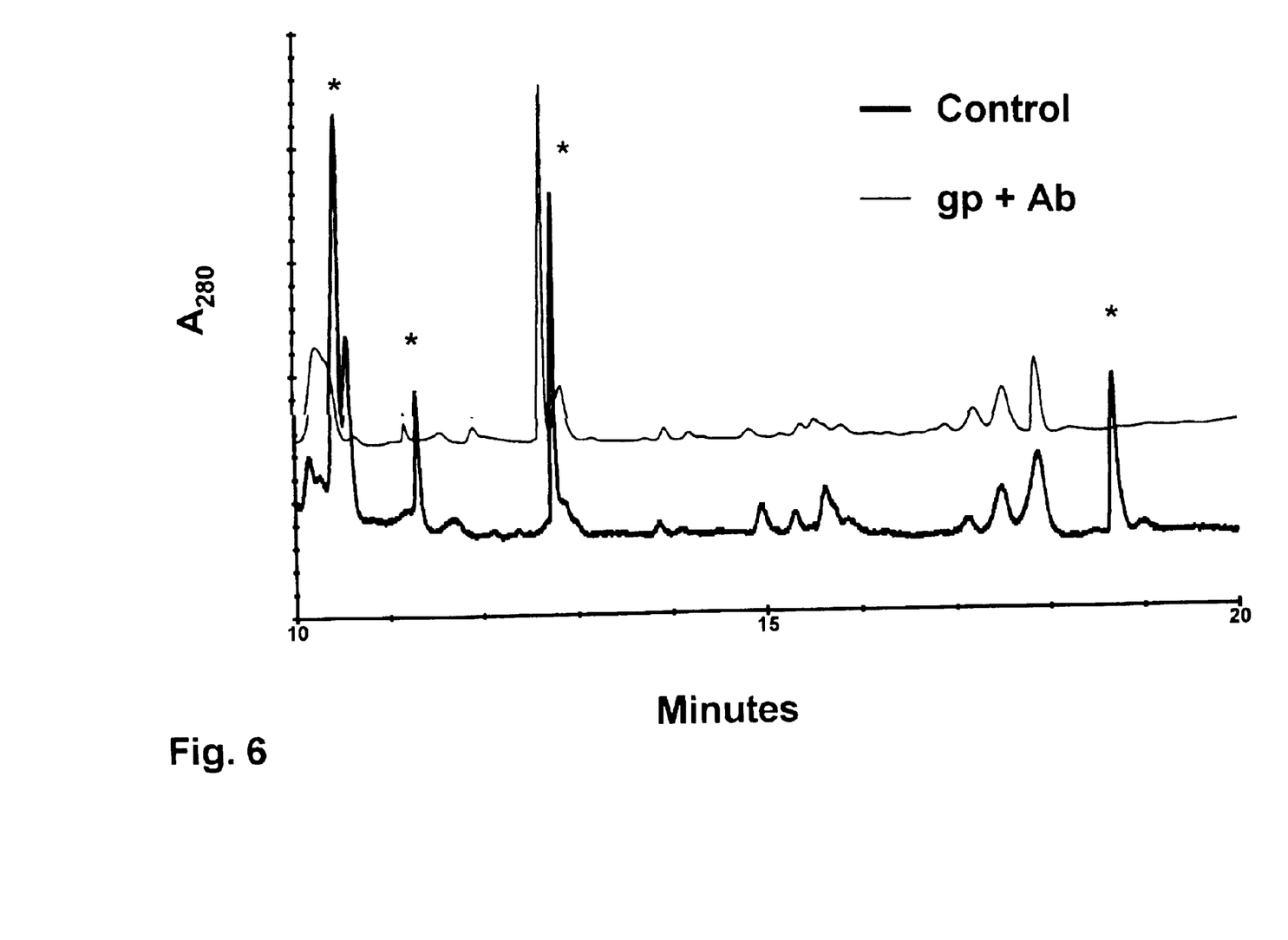
FIG. 6 shows incubation of the polyclonal antibody with a glycopeptide mixture produced by cleaving the rHuEPO with the peptidase chymotrypsin.

FIG. 6 shows the reaction of the antibody with chymotrypsin digested rHuEPO. The bottom trace shows the digested EPO while the top trace shows the results after antibody reaction. The goal of the experiment is to identify those glycopeptides which react with the antibody. The antibody adds new glycoprotein peaks and results in shifting or disappearance of EPO glycopeptide peaks. Therefore, the reacting glycopeptides are those that disappear or change greatly in level following antibody treatment. Those glycopeptides are marked with asterisks (*).

Figure 7:
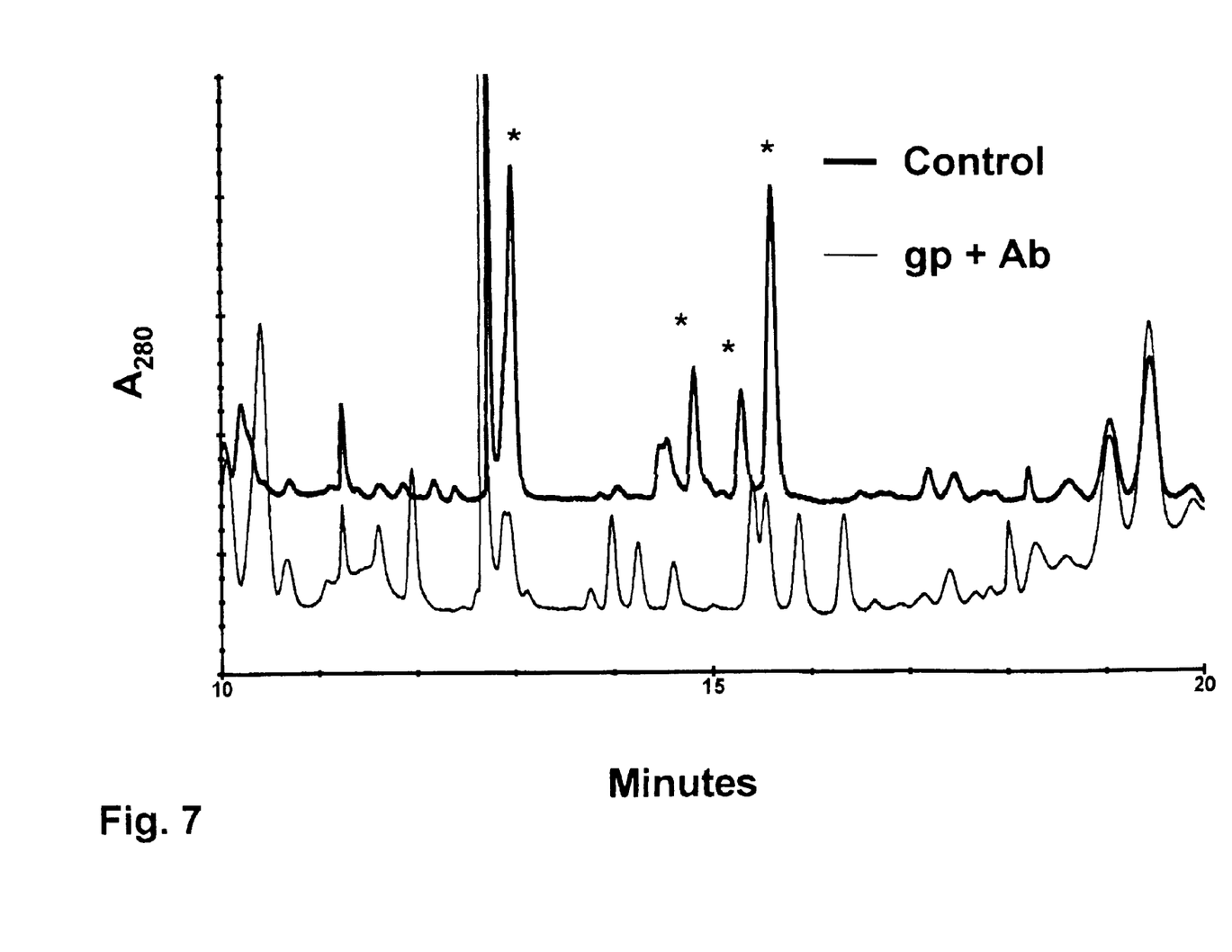
FIG. 7 shows incubation of the polyclonal antibody with a glycopeptide mixture produced by cleaving the rHuEPO with the peptidase trypsin.

FIG. 7 shows the reaction of the antibody with trypsin digested rHuEPO. The bottom trace shows the digested EPO while the top trace shows the results after antibody reaction. The goal of the experiment again is to identify those glycopeptides which show reactivity with the antibody. The antibody adds new glycoprotein peaks and results in shifting or disappearance of EPO peaks. Therefore, the reacting glycopeptides are those that disappear or change greatly in level following antibody treatment.

Figure 8:
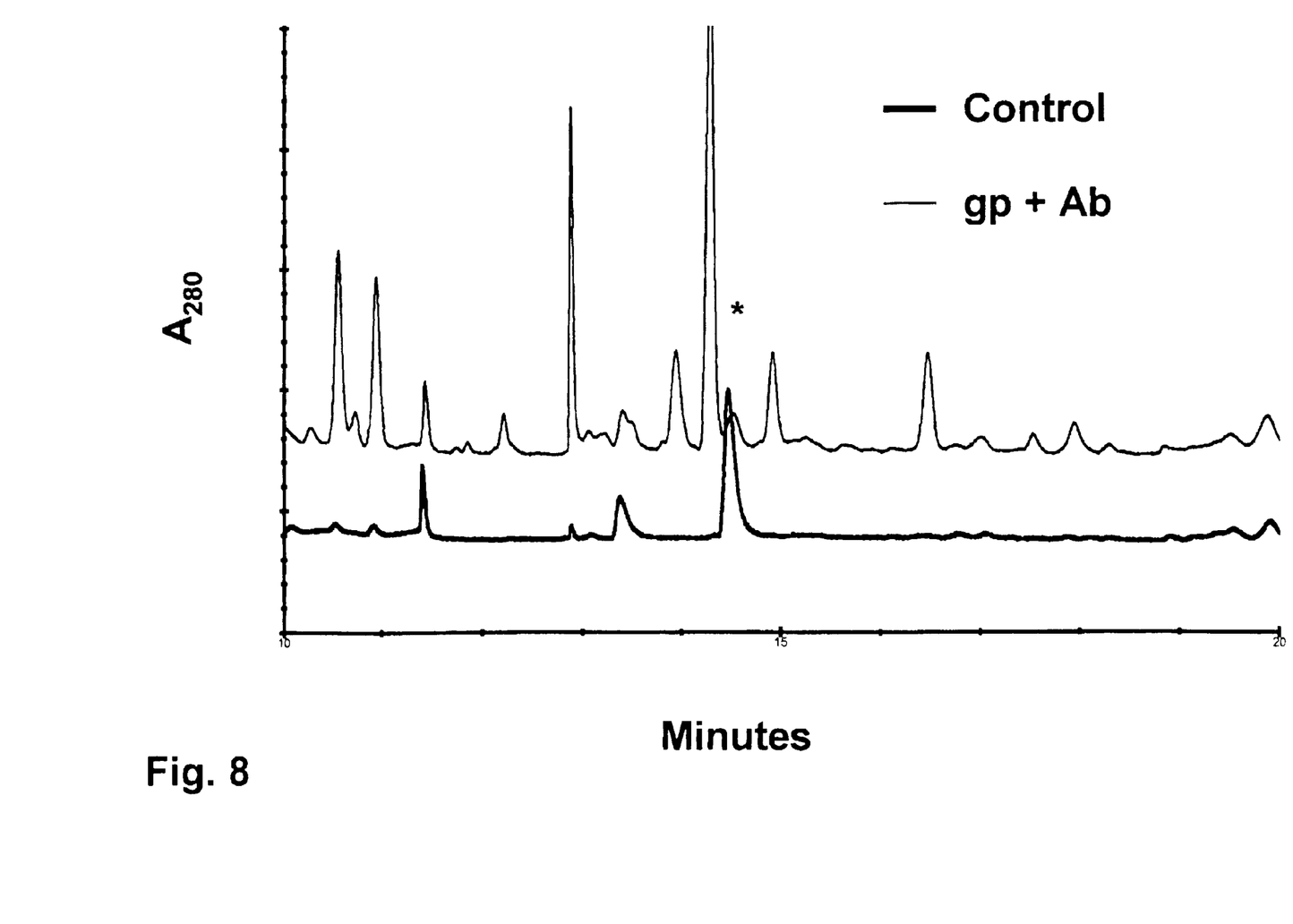
FIG. 8 shows incubation of the polyclonal antibody with a glycopeptide mixture produced by cleaving the rHuEPO with the peptidase Glu-c.

FIG. 8 shows the reaction of the antibody with Glu-c digested rHuEPO. The bottom trace shows the digested EPO while the top trace shows the results after antibody reaction. The goal of the experiment is to identify those glycopeptides which show reactivity with the antibody. The antibody adds new glycopeptide peaks and results in shifting or disappearance of EPO glycopeptide peaks. Therefore, the reacting glycopeptides are those that disappear or change greatly in level following antibody treatment. Those glycopeptides are marked with asterisks (*).

Figure 9:
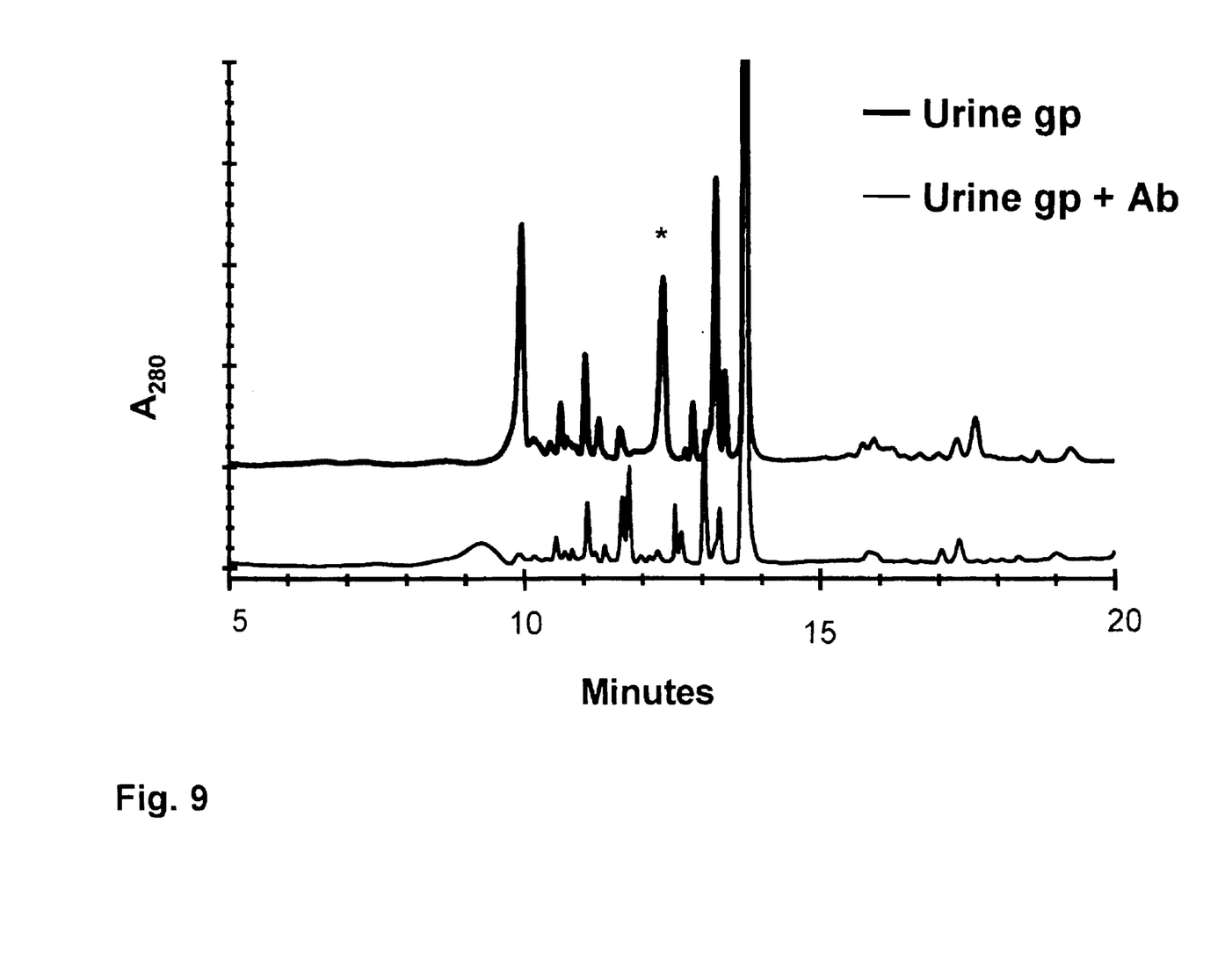
FIG. 9 shows glycopeptides from the urine of a patient undergoing treatment with EPO.

An important aspect of the present invention is its ability to detect rHuEPO in the urine of persons receiving treatment with the recombinant. Not only is this useful for avoiding abuse by athletes (this includes animal athletes such as dogs and horses as well as human athletes), it can also be used to monitor patients receiving EPO treatment. FIG. 9 shows the UV absorption profile of peptides purified by a 0–20% ammonium sulfate cut (e.g. the urine was brought to 20% saturation by adding saturated ammonium sulfate) from the urine of a patient undergoing EPO treatment. The precipitated proteins and peptides were digested with Glu-c and then separated by HPAEC-PAD (upper trace). An aliquot of the digested peptides were also treated with the rHuEPO specific polyclonal antibody. Several of the glycopeptides are altered by the antibody-of special note is glycopeptide a at a retention time of approximately 13 minutes.

The present invention demonstrates the methods to differentiate recombinant EPO from native EPO with antibodies. Now that the reactive peptides have been identified (particularly glycopeptide a FIG. 9, and the asterisk marked glycopeptides in FIGS. 6–8), individual glycopeptides unique to rHuEPO can be characterized by peptide mapping following removal of the carbohydrate by the enzyme N-Glycanase (PNGase F) which has been shown to completely release all N-linked oligosaccharide chains from rHuEPO.

The reactive glycopeptides unique to rHuEPO can then synthesized on a preparative scale to obtain sufficient quantity to be utilized as an antigen to obtain polyclonal or monoclonal antibodies using conventional methods. Alternatively, preparative quantities of these glycopeptides can be isolated from patient urine and used to generate monoclonal or polyclonal antibodies. Monoclonal antibodies thus generated are then screened to select those that do recognize rHuEPO or its fragments but do not recognize uHuEPO or its fragments. Antibodies reacting only with the specific glycopeptides can then be used to formulate ELISAs using conventional techniques. Polyclonal antibodies can be similarly purified by adsorption to remove any specificity to uHuEPO. While it is shown above that polyclonal antibodies to rHuEPO can be generated by direct use of rHuEPO as an antigen, use of the purified glycopeptides elicits a stronger immunological response and can be used to produce polyclonal antibodies with a much higher titer.

The present invention detects carbohydrate differences between recombinant and native human EPO through the use of antibodies. Standard immunization of a rabbit with recombinant EPO produces a polyclonal antibody capable of recognizing recombinant but not natural EPO. Furthermore, the polyclonal antibody recognizes distinct glycopeptides that can be produced by digesting recombinant EPO with peptidases. The polyclonal antibody also recognizes glycopeptides produced from recombinant EPO secreted by a patient being treated with EPO. The glycopeptides thus distinguished are useful as antigens for producing monoclonal antibodies or polyclonal antibodies specific to recombinant EPO. Conventional ELISA tests can be produced using these monoclonal or polyclonal antibodies or by using the original polyclonal antibody (produced by using rHuEPO as an antigen).

Thus the present invention comprises a method of discriminating recombinant EPO from native human EPO. This method works on intact EPO or on glycopeptides produced by degradation of the EPO. The preferred test uses a conventional ELISA test based on monoclonal antibodies to detect epitopes present in recombinant EPO or its breakdown products but not present in native EPO although polyclonal antibodies can also be used in an ELISA. Further, the methods described herein are directly adaptable to preparing antibodies for the detection of Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES CITED

1. Cowling, G. J. and Dexter, T. M., (1992) Erythropoietin and myeloid colony stimulating factors. *Trends in Biotechnology* 10:349–357.

2. Ekblom, B. and Berglund, B., (1991) Effect of erythropoietin administration on maximal aerobic power. *Scand. J. Med. Sci. Sports* 1:88–93.

3. Gareau, R., Brisson, G. R., Ayotte, C., Dube, J., and Caron, C., (1992) Erythropoietin Doping in Athletes: Possible Detection Through Measurement of Fibrinolytic Products. *Thrombosis and Haemostasis* 68:481482.

4. Eichner, E. R., (1992) Sports anemia, iron supplements, and blood doping. *Medicine and Science in Sports and Exercise* 24(9):S315–s318.

5. Weight, L. M., Alexander, D., Ellikon, T. and Jacobs, P. (1992) Erythropoietic adaptations to endurance training. *Eur. J. Appl. Physiol.* 64:444–448.

6. Ricci, G., Masotti, M., De Paoli Vitali, E., Vedovato, M. and Zanotti, G. (1988) Effects of Exercise on Haematologic Parameters, Serum Iron, Serum Ferritin, Red Cell 2,3-Diphosphoglycerate and Creatine Contents, and Serum Erythropoietin in Long-Distance Runners during Basal Training. *Acta Haemat.* 80:95–98.

7. Balaban, E. P. (1992) Sports Anemia., *Clinics in Sports Medicine* 11:313–325.

8. Berglund, B., Birgegard, G. and Hemmingsson, P., (1988) Serum erythropoietin in cross-country skiers. *Medicine and Science Sports and Exercise* 20:208–209.

9. Whitten, P. (1994) China's Short March to Swimming Dominance. *Swim,* January–February: 17–20.

10. Takeuchui, M. and Kobata, A., 1991. Structures and functional roles of the sugar chains of human erythropoietins, *Glycobiology* 1(4):337–346.

11. Takeuchi, M., Tasaki, S., Miyazaki, H., Kato, T., Hoshi, S., Kochibe, N. and Kobata, A. (1988) Comparative Study of the Asparagine-linked Sugar Chains of Human erythropoietins Purified from Urine and the Culture Medium of Recombinant Chinese Hamster Ovary Cells. *J. Biol. Chem.* 263:3657–3663.

12. Wasley, L. C., Timony, G., Murtha, P., Stoudemire, J., Domer, A. J., Caro, J., Krieger, M. and Kaufman, R. J., (1991) The Importance of N- and O-Linked Oligosaccharides for the Biosynthesis and In Vitro and In Vivo Biologic Activities of Erythropoietin. *Blood* 77:2624–2632.

13. Dube, S., Fisher, J. W., and Powell, J. S. (1988) Glycosylation at Specific Sites of Erythropoietin Is Essential for Biosynthesis, Secretion, and Biological Function. *J. Biol. Chem.* 263:17516–17521.

14. Hermentin, P., Witzel, R., Viegenthart, J. F. G., Kamerling, J. P., Nimtz, M., and Conradt, H. S., (1992) A strategy for the Mapping of N-Glycans by High-pH Anion Exchange Chromatography with Pulsed Amperometric Detection. *Analytical Biochemistry* 203:281–289.

15. Hokke, C. H., Kamerling, J. P., van Dedem, G. W. E. and Vliegenthart, J. F. G. (1991) Determination of the branch location of extra N-acetyllactosamine units in sialo N-Linked tetraantennary oligosaccharides. *FEBS LETTERS* 286:18–24.

16. Narhi, L. O., Arakawa, T., Aoki, K. H., Elmore, R., Rhode, M. F., Boone, T. and Strickland, T. W. (1991) The effect of Carbohydrate on the Structure and Stability of Erythropoietin. *J. Biol. Chem.* 266:23022–32026.

17. Rice, K. G., Takahashi, N., Namiki, Y., Tran, A. D., Lisi, P. J. and Lee, Y. C., (1992) Quantitative Mapping of the N-Linked Sialyloligosaccharides of Recombinant Erythropoietin: combination of Direct High-Performance Anion-Exchange Chromatography and 2-Aminopyridine Derivatization. *Anal. Biochem.* 206:278–287.

18. Sasaki, H., Bothner, B., Dell, A., and Fukuda, M., (1987) Carbohydrate Structure of Erythropoietin Expressed in Chinese Hamster Ovary Cells by a Human Erythropoietin cDNA. *J. Biol. Chem.* 262:12059–12076.

19. Stanley, P., 1992. Glycosylation engineering. *Glycobiology* 2(2):99–107.

20. Conradt, H. S., (1994) Carbohydrate Structures of Recombinant Glycoproteins from Mammalian and Insect Host Cell Lines. Lecture at The Second International glycobiology symposium: *Current Analytical Methods,* San Francisco, 2116194.

21. Tran, A. D., Park, S., Lisi, P. J., H., Oanh T., Ryall, R. R. and Lane, P. A., (1991). Separation of carbohydrate-mediated microheterogeneity of recombinant human erythropoietin by free solution capillary electrophoresis: Effects of pH, buffer type and organic additives. *Journal of Chromatography* 542:459–471.

22. Wide, L. and Bengtsson, C., (1990) Molecular charge heterogeneity of human serum erythropoietin. *British Journal of Haematology* 76:121–127.

23. Salmonson, T., (1990). Pharmacokinetic and Pharmacodynamic Studies on Recombinant Human Erythropoietin, *Scand. J. Urology and Nephrology,* Supp. 129.

24. Watson, E. and Bhide, A., 1993. Carbohydrate Analysis of Recombinant-Derived Erythropoietin, *LC-GC* 11(3) :216–220.

25. Wognum, A. W., Lansdorp, P. M. and Krystal, G., (1990) Immunochemical Analysis of Monoclonal Antibodies to Human Erythropoietin, *Exp. Hematol.* 18:228–233.

26. Wognum, A. W., Lansdorp, P. M., Eaves, C. J. and Krystal, G. (1988) Use of a Sensitive Bioimmunoadsorbent Assay to Isolate and Characterize Monoclonal Antibodies to Biologically Active Human Erythropoietin. *Blood* 71:1731–1737.

27. Sytkowski, A. J. and Donahue, K. A., (1987) Immunochemical Studies of Human Erythropoietin Using Site-specific Anti-peptide Antibodies: Identification of a Functional Domain. (1987) *J. Biol. Chem.* 262:1161–1165.

I claim:

1. A method of detecting in a body fluid of a mammal a recombinant erythropoietin produced by cells of species different from the mammal, wherein the cells are CHO cells, comprising the steps of:

raising heterologous antibodies to the recombinant erythropoietin produced in CHO cells wherein the antibodies bind to a carbohydrate-containing epitope present on the recombinant erythropoietin but not present on erythropoietin produced by the mammal and wherein the antibodies do not bind to erythropoietin produced by the mammal;

contacting a body fluid of the mammal with the antibodies under conditions sufficient to allow binding of the antibodies; and detecting binding of the antibodies wherein binding of said antibodies is indicative of presence of the recombinant erythropoietin in the mammal.

2. The method of claim 1, wherein the body fluid is urine.

* * * * *